(12) United States Patent
Joseph-Ridge

(10) Patent No.: US 8,841,333 B2
(45) Date of Patent: Sep. 23, 2014

(54) METHODS FOR TREATING NEPHROLITHIASIS

(75) Inventor: Nancy Joseph-Ridge, Highwood, IL (US)

(73) Assignee: Takeda Pharmaceuticals U.S.A., Inc., Deerfield, IL (US)

(*) Notice: Subject to any disclaimer, the term of this patent is extended or adjusted under 35 U.S.C. 154(b) by 0 days.

(21) Appl. No.: 11/429,734

(22) Filed: May 8, 2006

(65) Prior Publication Data

US 2006/0252808 A1 Nov. 9, 2006

Related U.S. Application Data

(60) Provisional application No. 60/678,987, filed on May 9, 2005.

(51) Int. Cl.
*A61K 31/425* (2006.01)
*A61K 31/426* (2006.01)
*A61K 31/415* (2006.01)

(52) U.S. Cl.
CPC ............. *A61K 31/415* (2013.01); *A61K 31/426* (2013.01)
USPC .......................................... 514/365; 514/366

(58) Field of Classification Search
USPC ................................. 514/365, 366
See application file for complete search history.

(56) References Cited

U.S. PATENT DOCUMENTS

| | | | |
|---|---|---|---|
| 4,058,614 A | 11/1977 | Baldwin | |
| 4,156,732 A | 5/1979 | Lang | |
| 4,296,122 A | 10/1981 | Cragoe | |
| 4,510,322 A | 4/1985 | Blaine | |
| 4,632,930 A | 12/1986 | Carini et al. | |
| 5,268,386 A | 12/1993 | Harada et al. | |
| 5,358,961 A | 10/1994 | Lee et al. | |
| 5,514,681 A | 5/1996 | Wren | |
| 5,614,520 A | 3/1997 | Kondo et al. | |
| 5,693,818 A | 12/1997 | Von Unge | |
| 5,770,601 A | 6/1998 | Wren | |
| 5,883,137 A | 3/1999 | King | |
| 5,965,625 A * | 10/1999 | King | 424/773 |
| 6,015,829 A | 1/2000 | Ishibuchi et al. | |
| 6,037,344 A | 3/2000 | Wren | |
| 6,225,474 B1 | 5/2001 | Matsumoto et al. | |
| 6,281,222 B1 | 8/2001 | Salzman et al. | |
| 6,569,862 B1 | 5/2003 | Marban | |
| 7,074,816 B2 | 7/2006 | Nakamura et al. | |
| 2002/0019360 A1 | 2/2002 | Kivlighn | |
| 2002/0187120 A1 | 12/2002 | Holmes-Farley et al. | |
| 2003/0039627 A1 | 2/2003 | Holmes-Farley et al. | |
| 2003/0186998 A1 | 10/2003 | Marban | |
| 2004/0121004 A1 | 6/2004 | Taneja | |
| 2004/0122067 A1 | 6/2004 | Zhao | |
| 2004/0131676 A1 | 7/2004 | Taneja | |
| 2005/0070552 A1 | 3/2005 | Fedida et al. | |
| 2006/0040945 A1 | 2/2006 | Smolka et al. | |
| 2007/0167454 A1 | 7/2007 | Lademacher | |
| 2008/0269226 A1 | 10/2008 | Lademacher | |
| 2009/0042887 A1 | 2/2009 | Lademacher et al. | |
| 2009/0124623 A1 | 5/2009 | Lademacher et al. | |
| 2010/0311756 A1 | 12/2010 | Zhao | |
| 2012/0065207 A1 | 3/2012 | Gunawardhana | |
| 2012/0065215 A1 | 3/2012 | Gunawardhana | |
| 2012/0065236 A1 | 3/2012 | Gunawardhana | |
| 2013/0143886 A1 | 6/2013 | Lademacher et al. | |

FOREIGN PATENT DOCUMENTS

| | | |
|---|---|---|
| DE | 2707268 | 8/1978 |
| DE | 2707269 | 8/1978 |
| DE | 2707270 | 8/1978 |
| DE | 3112116 | 11/1982 |
| EP | 0000128 | 1/1979 |
| EP | 0104483 | 4/1984 |
| EP | 0415566 | 6/1991 |
| EP | 0779074 | 6/1997 |
| EP | 0936217 | 8/1999 |
| GB | 2031882 | 4/1980 |
| JP | 7-242694 | 9/1995 |
| JP | 11-140086 | 5/1999 |
| JP | 2002105067 | 4/2002 |
| WO | WO 92/09279 | 6/1992 |
| WO | WO 93/04688 | 3/1993 |
| WO | WO 96/26208 | 8/1996 |
| WO | WO 99/24038 | 5/1999 |
| WO | WO 00/07193 | 2/2000 |
| WO | WO 00/07629 | 2/2000 |
| WO | WO 00/27394 | 5/2000 |
| WO | WO 01/12204 | 2/2001 |
| WO | WO 02/00210 | 1/2002 |
| WO | 02/062330 | 8/2002 |

(Continued)

OTHER PUBLICATIONS

Heilberg et al.; "Renal Stone Disease: Causes, Evaluation and medical Treatment"; 2006; Arquivos Brasileiros de Endocrinologia Metabologia; 50(4); 823-31.*
Horiuchi, et al.; "A comparative study on the hypouricemic activity and potency in renal xanthine calculus formation of two xanthine oxidase/xanthine dehydrogenase inhibitors: TEI-6720 and allopurinol in rats"; 1999; 104(3): 307-319; PubMed abstract; PMID: 10741381.*
Pittman; "Diagnosis and management of gout"; 1999; American Family Physician; 59(7): 1799; Proquest text version, pp. 1-7.*
Horiuchi, et al.; "A comparative study on the hypouricemic activity and potency in renal xanthine calculus formation of two xanthine oxidase/xanthine dehydrogenase inhibitors: TEI-6720 and allopurinol in rats"; 1999; 104(3): 307-319.*

(Continued)

*Primary Examiner* — Paul Zarek
*Assistant Examiner* — George W Kosturko
(74) *Attorney, Agent, or Firm* — Michael Best & Friedrich LLP

(57) ABSTRACT

The present invention relates to methods of treating subjects suffering from nephrolithiasis by administering to a subject in need of treatment thereof a therapeutically effective amount of at least one xanthine oxidoreductase inhibiting compound or salt thereof.

2 Claims, No Drawings

(56) References Cited

FOREIGN PATENT DOCUMENTS

| WO | WO 03/037332 | 5/2003 |
|---|---|---|
| WO | WO 03/064410 | 8/2003 |
| WO | WO 2004/009563 | 1/2004 |
| WO | WO 2006/028342 | 3/2006 |
| WO | WO 2006/055412 | 5/2006 |
| WO | WO 2007/019153 | 2/2007 |
| WO | WO 2008/089296 | 7/2008 |
| WO | WO 2009/041798 | 4/2009 |
| WO | WO 2010/030988 | 3/2010 |

OTHER PUBLICATIONS

Itoh, Y. et al., Journal of Urology vol. 173 pp. 271-275. Published Jan. 2005.*
Aucamp, J. et al. Anticancer Research vol. 17, pp. 4381-4386. Published 1997.*
Sonoda, T., et al. Hinyokika Kiyo vol. 31, pp. 2071-2079. Published 1985. English Abstract provided.*
Laakso, J.T. et al., Journal of Hypertension vol. 22, pp. 1333-1340. Published 2004.*
Okamoto, K. et al., Journal of Biological Chemistry vol. 278, pp. 1848-1855. Published 2003.*
Horiuchi, H. et al., Research Communications in Molecular Pathology and Pharmacology vol. 104, pp. 307-319. Published 1999.*
Reagan-Shaw, S. et al., FASEB J vol. 22, pp. 659-661. Published 2007.*
Database CAPLUS on STN Online, No. 1967:481058, Zoellner, N. "Treatment of Gout and Urate Nephrolithiasis with Allopurinol", abstract, Verhandlungen der Deutschen Gesellschaft fuer Innere Medizin, 1967, vol. 72, pp. 781-784.
Database CAPLUS on STN Online, No. 2001:223439, Yasui et al. "Effects of Allopurinol on Renal Stone Formation and Osteopontin Expression in a Rat Urolithiasis Model", abstract, Nephron, 2001, vol. 87, No. 2, pp. 170-176.
Database CAPLUS on STN Online, No. 1967:410278, Zoellner et al. "Allopurinol in the Treatment of Gout and Uric Acid Nephrolithiasis", abstract, Deutsche Medizinische Wochenschrift, 1967, vol. 92, No. 14, pp. 654-660.
JC Lieske et al., Kidney International, 69: 760-764 (2006).
Zoellner, N. "Treatment of Gout and Urate Nephroliathiasis with Allopurinol" Abstract, Verhandlungen der Deutschen Gesellschaft fuer lnnere Medizin, vol. 72, pp. 781-784 (1967).
Yasui et al., "Effects of Allopurinol on Renal Stone Formation and Osteopontin Expression in a Rat Urolithiasis Model" Abstract Nephron, 2001, vol. 87, No. 2, pp. 170-176.
Zoellner et al. "Allopurinol in the Treatment of Gout and Uric Acid Nephrolithiasis" abstract, Deutsche Medizinische Wochenschrift, 1967, vol. 92, No. 14, pp. 654-660.
Allopurinol Drugdex Drug Evaluations, Thompson Micromedix, 2006, 52 pages.
Antiplatelet Trialists Collaboration et al., Collaborative overview of randomised trials of antiplatelet therapy- I Prevention of death, myocardial infarction, and stoke by prolonged antiplatelet therapy in various categories of patients, BMJ vol. 308, pp. 81-106, Jan. 8, 1994.
Anzai et al., Renal Urate Handling: Clinical Relevance of Recent Advances, Current Science Inc. Copyright 2005, pp. 227-234.
Arakawa et al., Allopurinol Hypersensitivity Syndrome Associate with Systemic Cytomegalovirus Infection and Systemic Bacteremia, International Medicine vol. 40, No. 4, pp. 331-335 (Apr. 2001).
Arellano et al., Allopurinol Hypersensitivity Syndrome—A Review, The Annals of Pharmacotherapy, vol. 27, pp. 337-341, Mar. 1993.
Arromdee et al., Epidemiology of Gout—Is the Incidence Rising, the Journal of Rheumatology 2002; 29:11, pp. 2403-2406.
Baker et al., Serum uric acid and cardiovascular disease: Recent Development, and where do they leave us? The American Journal of Medicine, vol. 118 No. 8, pp. 816-826, Aug. 2005.
Becker et al., Clinical Aspects of Monosodium Urate Monohydrate Crystal Deposition Disease (Gout). Rheumatic Disease Clinics of North America—vol. 14, No. 2, pp. 377-395, Aug. 1988.

Becker et al., We can make Gout Management more successful now, Current Opinion in Rheumatology, vol. 20, pp. 167-172, 2008.
Becker, M. et al., "A Phase 3 Randomized, Controlled, Multicenter, Double-Blind Trial (RCT) Comparing Efficacy and Safety of Daily Febuxostat (FEB) and Allopurinol (ALLO) in Subjects with Gout" [abstract], Amer College Rheum. (2008) Abstract No. L11.
Becker, M.A. et al., A phase 3 study comparing the safety and efficacy of oral febuxostat and allopurinol in subjects with hyperuricemia and gout [abstract]. Arthritis Rheum. Dec. 2004; 50(12):4103-4104. Abstract No. L18.
Becker, M.A. et al., "A safety and efficacy clinical trial of a novel non-purine selective inhibitor of xanthine oxidase, febuxostat in subjects with gout" [abstract]. Ann Rheum Dis. Jul. 2004; 63(Suppl 1):60. Abstract No. OP0007.
Becker, M.A. et al., "Allopurinol intolerant patients treated with febuxostat for 4 years" [abstract]. Arthritis Rheum. Sep. 2006; 54(9 Suppl):S646-S647. Abstract No. 1605.
Becker MA et al., Clinical efficacy and safety of successful long-term urate lowering with febuxostat or allopurinol in subjects with gout. J Rheumatol. (2009) 36(6):1273-1282.
Becker, M.A. et al., Determinants of the clinical outcomes of gout during the first year of urate-lowering therapy. Nucleosides Nucleotides and Nucleic Acids. Jun. 2008; 27(6):585-591.
Becker, M.A. et al., Febuxostat (TMX-67), a novel, non-purine, selective inhibitor of xanthine oxidase, is safe and decreases serum urate in healthy volunteers. Nucleosides Nucleotides Nucleic Acids. Oct. 2004; 23(8 & 9):1111-1116.
Becker MA et al., Febuxostat compared with allopurinol in patients with hyperuricemia and gout, N Engl J Med. Dec. 2005;353(23):2450-2461.
Becker, M.A. et al., "Febuxostat vs allopurinol controlled trial in subjects with hyperuricemia and gout (FACT): a multicenter, phase 3, randomized, controlled, double-blind clinical study" [abstract]. Pharmacotherapy Oct. 2005; 25(10):1488. Abstract No. 359E.
Becker MA et al., Febuxostat, a novel non-purine selective inhibitor of xanthine oxidase, therapy in allopurinol intolerant patients [abstract]. Arthritis Rheum. Sep. 2004;50(9 Suppl):S336. Abstract No. 803.
Becker, M.A. et al., "Febuxostat, a novel nonpurine selective inhibitor of xanthine oxidase, therapy in allopurinol intolerant patients" [abstract]. J Natl Med Assoc. Jun. 2005; 97(6):894.
Becker MA et al., Febuxostat, a novel nonpurine selective inhibitor of xanthine oxidase: a twenty-eight-day, multicenter, phase II, randomized, double-blind, placebo-controlled, dose-response clinical trial examining safety and efficacy in patients with gout. Arthritis Rheum. Mar. 2005;52(3):916-923.
Becker MA et al., Gout flare incidence in relation to average serum urate during the first year of urate-lowering therapy [abstract]. Arthritis Rheum. Sep. 2007;56 (9 Suppl):S322-S323. Abstract No. 758.
Becker MA et al., Long-term urate-lowering therapy in subjects with gout—the EXCEL study [abstract]. International Journal of Rheumatic Diseases. 2008;11 (Suppl 1):A209. Abstract No. P1Q-07.
Becker MA et al., Magnetic resonance imaging (MRI) in the quantitative assessment of gouty tophi [abstract]. Arthritis Rheum. Sep. 2003;48(9 Suppl):S528. Abstract No. 1344.
Becker, M.A. et al., "Magnetic resonance imaging of gouty tophi during treatment with febuxostat, a nonpurine selective inhibitor of xanthine oxidase" [abstract]. J Natl Med Assoc. Jun. 2005; 97(6):883.
Becker MA et al., Reduction in gout flares in subjects with chronic gout treated with febuxostat or allopurinol for 52-weeks: FACT trial [abstract]. Arthritis Rheum. Sep. 2005;52(9 Suppl):S108. Abstract No. 202.
Becker, M.A. et al., "The long-term clinical benefits of febuxostat vs allopurinol in subjects with gout: interim analysis of the EXCEL trial, an ongoing phase 3, open-label extension study" [abstract]. Ann Rheum Dis. Jul. 2006; 65(Suppl 2):431. Abstract No. FRI0484.
Becker MA et al., Urate-lowering pharmacotherapy with febuxostat (FEB) or allopurinol (ALLO) in African-American subjects with gout [abstract]. Arthritis Rheum. Sep. 2007;56(9 Suppl):S637. Abstract No. 1622.

(56) References Cited

OTHER PUBLICATIONS

Becker, M.A. et al., "Urate-lowering pharmacotherapy with febuxostat or allopurinol in black-american subjects with gout" [abstract]. Ann Rheum Dis. Jul. 2007; 66(Suppl II):231. Abstract No. THU0340.
Becker, M.A. et al., "Urate-lowering therapy (Febuxostat [FEB] or Allopurinal [ALLO]) in subjects with gout: interim results from the febuxostat comparative extension long-term study (EXCEL)" [abstract]. Ann Rheum Dis. Jul. 2007; 66(Suppl II):230-231. Abstract No. THU0339(757).
Beers, M.H. et al. "221 / Urinary Calculi," The Merck Manual of Diagnosis and Therapy, (1999) pp. 1838-1840.
Berge et al., "Pharmaceutical salts," J. Pharm. Sci. (1977) 66:1-19.
Berry, C.E. et al., "Xanthine oxidoreductase and cardiovascular disease: molecular mechanisms and pathophysiological implications", J Physiol (2004), 555.3:589-606.
BOF-4272, Drug Print Report, Printed from Website http://release2.id.../report. print_disply?_query_id=1214721&template=DrugPrint&id=852, Jan. 17, 2003.
Borstad et al., Colchicine for Prophylaxis of Acute Flares When Initiating Allopurinol for Chronic Gouty Arthritis, The Journal of Rheumatology 2004, 31:12, pp. 2429-2432.
Braunwald, Biomarkers in Heart Failure, N Eng J Med 358;20, pp. 2148-2148 www.nejm.org May 15, 2008, Downloaded from www.nejm.org at Abbott on May 21, 2008. Copyright 2008 Massachusetts Medical Society.
Burrell, L.M. "A Risk-Benefit Assessment of Losartan Potassium in the Treatment of Hypertension," Drug Safety (1997) 16(1):56-65.
Carter, J.D. et al., An analysis of MRI and ultrasound imaging in patients with gout who have normal plain radiographs, Rheumatology vol. 48, pp. 1442-1446, Sep. 10, 2009.
Chao et al., Hypersensitivity Syndrome and Pure Red Cell Aplasia Following Allopurinol Therapy in Patent with Chronic Kidney Disease, The Annals of Pharmacotherapy, vol. 39, pp. 1552-1556, Sep. 2005.
Chen et al., Diagnosis and Management of Gout, JCOM, vol. 10 No. 6, pp. 336-343, Jun. 2003.
Chobanian, A.V. et al., The Seventh Report of the Joint National Committee on Prevention, Detection, Evaluation, and Treatment of High Blood Pressure, U.S. Department of Health and Human Services, NIH Publication No. 04-5230, Aug. 2004, JAMA (2003) 289(19):2560-2572.
Choi et al., Independent Impact of Gout on Mortality and Risk for Coronary Heart Disea0se,America Heart association, Journal of the American Heart Association, vol. 116, pp. 894-900, Aug. 13, 2007.
Choi, Epidemiology of Crystal Arthropathy, Rheumatic Disease Clinic of North America, vol. 32, pp. 255-273, (2006).
Chonchol et al., Relationship of Uric Acid with Progression of Kidney Disease, American Journal of Kidney Diseases, vol. 50, No. 2, pp. 239-247, Aug. 2007.
Cingolani et al., J. Cardiac Failure (2006) 12(7):491-498.
Cirillo et al., Uric Acid, the Metabolic Syndrome, and Renal Disease, Journal of the American Society of Nephrology, vol. 17, pp. S165-S168, 2006.
Cockcroft et al., Prediction of Creatinine Clearance from Serum Creatinine, Nephron, vol. 16, pp. 31-41, 1976.
Cooper, N. et al., "Quantification of uric acid, xanthine and hypoxanthine in human serum by HPLC for pharmacodynamic studies." J Chromatogr B, (2006); 837:1-10.
Daghini, E. et al., Acute inhibition of the endogenous xanthine oxidase improves renal hemodynamics in hypercholesterolemic pigs. Am. J. Physiol. Regul. Integr. Comp. Physiol., Mar. 2006, vol. 290, pp. R609-R615.
Dalbeth at al., Computed Tomography Measurement of Tophus, Arthritis & Rheumatism (Arthritis Care and Research), vol. 57, No. 3, pp. 461-465, Apr. 15, 2007.
Dalbeth et al., Dose Adjustment of Allopurinol According to Creatinine Clearance Does Not Provide Adequate Control of Hyperuricemia in Patients with Gout, The Journal of Rheumatology, 33:8, pp. 1646-1649, 2006.

Day et al., Allopurinol dosage selection: relationship between dose and plasma oxipurinol and urate concentrations and urinary urate excretion, Br. J. Clin Pharmac: pp. 423-428, 1988.
Delorme, N. et al., "Interaction of allopurinol and theophylline," Pharm. Clin. Therapeutique (1987) 26(6):403-404.
Drug and Therapeutics Bulletin, "Gout in Primary Care," (2004) BNF 10.1.1 & 10.1.4, p. 37-40.
Edwards, Management of Hyperuricemia, vol. 115, pp. 2314-238.
Elenbaas, R.M. et al., "Prediction of serum theophylline levels," Annals Emergency Medicine (1984) 13(2):92-96 (Abstract).
Emmerson, Drug Therapy—The Management of Gout, The New England Journal of Medicine, vol. 334 No. 7, pp. 445-451, Feb. 15, 1996.
Engberding et al., Circulation (2004) 110:2175-2179.
Fam et al., Desensitization to Allopurinol in Patients with Gout and Cutaneous Reactions, The American Journal of Medicine, vol. 93, pp. 299-301, Sep. 1992.
Fam et al., Efficacy and Safety of Desensitization to Allpourinol Following Cutaneous Reactions, Arthritis & Rheumatism, vol. 44, No. 1, pp. 231-238, Jan. 2001.
Fam, Alternate Urate-Lowering Drugs and the Management of Hyperuricemia in Allopurinol-Intolerant Patients, International Journal of Advances in Rheumatology, vol. 1 No. 4, pp. 122-130, 2003.
Fam, Difficult Gout and New Approaches for Control of Hyperuricemia in the Allopurinol-Allergic Patient, Sunnybrook and Women's College Health Science Center, 3:29-35, 2001.
Fang et al, Serum Uric Acid and Cardiovascular Mortality, The NHANES I Epidemiology Follow-Up Study, 1971-1992, JAMA, vol. 283 No. 18, pp. 2404-2410, May 10, 2000.
Feig et al., Serum Uric Acid—A Risk Factor and a Target for Treatment?, J Am Soc Nephrol, vol. 17, pp. S69-S73, 2006.
Fukunari, A. et al., "Y-700 [1-[3-Cyano-4-(2,2-dimethylpropoxy)phenyl]-1$H$-pyrazole-4-carboxylic Acid]: A Potent Xanthine Oxidoreductase Inhibitor with Hepatic Excretion," The Journal of Pharmacology and Experimental Therapeutics, (2004) 311(2):519-528.
Fyfe et al., Kinetic Properties and Inhibition of Ortidine 5'-Phosphate Decarboxylase, The Journal of Biological Chemistry, vol. 248, No. 11, pp. 3801-3809, 1973.
Garbe et al., Exposure to Allopurinol and the Risk of Cataract Extraction in Elderly Patients, Arch Ophthalmol, vol. 116, pp. 1652-1656, Dec. 1998.
Gibson et al., Renal Impairment and Gout, Annals of Rheumatic Diseases, 39, pp. 417-423, 1980.
Gibson, T. et al., "Tienilic Acid in the Treatment of Gout and Hypertension," Purine Metabolism in Man-III, vol. 122A (1980) 277-282.
Grabowski B et al., Effect of hydrochlorothiazide on pharmacokinetics and pharmacodynamics of febuxostat [abstract]. Arthritis Rheum. Sep. 2005;52(9 Suppl):S103-S104. Abstract No. 190.
Grabowski, B. et al., Pharmacokinetics, pharmacodynamics, and safety of febuxostat (TMX-67), a non-purine selective inhibitor of xanthine oxidase, in healthy subjects [abstract]. J Clin Pharmacol. Oct. 2004; 44(10):1196. Abstract No. 47.
Grabowski, B. A. et al., "Metabolism and Excretion of [$^{14}$C] Febuxostat, a Novel Nonpurine Selective Inhibitor of Xanthine Oxidase, in Healthy Male Subjects." J Clin Pharmacol (2010) 51(2):189-201.
Graessler et al., Association of the Human Urate Transporter 1 with Reduced Renal Uric Acid Excretion and Hyperuricemia in a German Caucasian Population, Arthritis @ Rheumatism, vol. 54, No. 1, pp. 292-300, Jan. 2006.
Gutierrez-Macias et al., Fatal Allopurinol Hypersensitivity syndrome after treatment of asymptomatic hyperuricemia, BMJ vol. 331, pp. 623-624, Sep. 17, 2005.
Gwinner et al., Pivotal role of xanthine oxidase in the initiation of tubulointerstitial renal injury in rats with hyperlipidemia, Kidney International, vol. 69, No. 3, pp. 481-487, 2006.
Halevy et al., Allopurinol is the most common cause of Stevens-Johnson syndrome and toxic epidermal necrolysis in Europe and Israel, J Am ACAD Dermatol, pp. 25-32, Jan. 2008.
Hande et al., Severe Allopurinol Toxicity Description of Guidelines for prevention on Patients with Renal Insufficiency, The American Journal of Medicine, vol. 76, pp. 47-76, Jan. 1984.

(56) References Cited

OTHER PUBLICATIONS

Herschfield, M.J. "Gout and uric acid metabolism," Textbook of Medicine, 21st Edition vol. 2, pp. 1541-1548.
Hjortnaes et al., Serum Uric Acid is a Strong Predictor for Stroke in Patients with Metabolic Syndrome, 34:9, pp. 1882-1187, 2007.
Holder et al., Cutaneous and Systemic Manifestations of Drug-Induced Vacuities, The Annals of Pharmacotherapy, vol. 36, pp. 130-147, Jan. 2002.
Horiuchi, H. et al., "Allopurinol increases ear swelling and mortality in a dinitrofluorobenzene-induced contact hypersensitivity mouse model." Biol Pharm Bull (1999) 22(8):810-815.
Horiuchi, H. et al., "Allopurinol induces renal toxicity by impairing pyrimidine metabolism in mice." Life Sci (2000) 66(21):2051-2070.
Horiuchi, H. et al., "Hypouricemic activity of a novel xanthine oxidase/xanthine dehydrogenase (XOD/XDH) inhibitor, TE1-6720 in rats" [abstract]. Jpn J Pharmacol. 2000; 82(Suppl 1):271P. Abstract No. P-606.
Horiuchi, H. et al., "Nephrotoxic effects of allopurinol in dinitrofluorobenzene-sensitized mice: Comparative studies on TEI-6720." *Res Commun Mol Pathol Pharmacol* 1999; 104(3):293-305.
Hoshide S et al., Metabolites of TMX-67, a new pharmaceutical entity for the treatment of gout or hyperuricemia, and their pharmacokinetic profiles in humans [abstract].Drug Metab Rev. 2000;32(Suppl 2):269. Abstract No. 266.
Hoshide, S. et al., "PK/PD and safety of a single dose of TMX-67 (febuxostat) in subjects with mild and moderate renal impairment." Nucleosides Nucleotides Nucleic Acids. Oct. 2004; 23(8-9):1117-1118.
Hou, M. et al., "Acute effects of febuxostat, a nonpurine selective inhibitor of xanthine oxidase, in pacing induced heart failure." J Cardiovasc Pharmacol (2006) 48(5):255-263.
Hung et al., HBL-B 5801 allele as a genetic marker for severe cutaneous adverse reactions caused by allopurinol, PNAS, vol. 102, No. 11, pp. 4134-4139, Mar. 15, 2005.
Hydroxyakalone, Drug Print Report, http://release2..i.../reports.print_display?i_query_id=121472&templates=DrugPrint &id=2091, Jan. 17, 2003, 2 pages.
Ioachimescu et al., Serum Uric Acid is an Independent Predictor of All-Cause Mortality in Patients at High Risk of Cardiovascular Disease, Arthritis & Rheumatism, vol. 58 No. 2, pp. 623-630, Feb. 2008.
Iseki et al., Significance of Hyperuricemia as a Risk Factor for Developing ESRD in a Screened Cohort, American Journal of Kidney Disease, vol. 44, No. 4, pp. 642-650, Oct. 2004.
Iseki et al.,Significance of Hyperuricemia on the Early Detection of Renal Failure in a Cohort of Screened Subjects, Hypertens Res., vol. 24, No. 6, pp. 691-697, 2001.
Ishibuchi, S. et al., "Synthesis and structure—activity relationships of 1-phenylpyrazoles as xanthine oxidase inhibitors," Bioorg Med Chem Lett (2001) 11(7):879-882.
Ishiwata Y et al., TMX-67 a novel xanthine oxidase/xanthine dehydrogenase (XOD) inhibitor, shows strong uric acid lowering action in patients with hyperuricemia and gout [abstract]. Arthritis Rheum. Sep. 2001;44(Suppl 9):S129. Abstract No. 459.
Jeske et al., In vitro Profiling of the Effects of Febuxostat on Hemostatic Parameters, Hemostasis Research laboratories, Dec. 28, 2005, 22 pages.
Jordan, N. et al., "Febuxostat: a safe and effective therapy for hyperuricemia and gout", Future Rheumatology, (2006) 1(3):303-309.
Joseph-Ridge, N., Phase II, dose-response, safety and efficacy clinical trial of a new oral xanthine oxidase inhibitor TMX-67 (febuxostat) in subjects with gout [abstract]. Arthritis Rheum. Sep. 2002; 46(9 Suppl):S142. Abstract No. 289.
Jungers, et al., ESRD Caused by Nephrolithaisis—Prevalence, Mechanisms, and Prevention, American Journal of Kidney Diseases, vol. 44, No. 5, pp. 691-805, Nov. 2004.
Kamatani, N. et al., "Febuxostat, a novel non-purine selective inhibitor of xanthine oxidase, in a phase III placebo-controlled double-blind clinical trial in Japanese subjects with gout or hyperuricemia" [abstract]. Arthritis Rheum. Sep. 2004; 50(9 Suppl):S337. Abstract No. 805.
Kamatani, N. et al., "Febuxostat, a novel non-purine selective inhibitor of xanthine oxidase, in a phase III placebo-controlled double-blind clinical trial with gout or hyperuricemia" [in Japanese] [abstract]. Gout and Nucleic Acid Metabolism. 2005; 29(1):68.
Kamatani, N. et al., "Febuxostat, a novel non-purine selective inhibitor of xanthine oxidase, in an allopurinol-controlled phase III clinical trial in Japanese subjects with gout or hyperuricemia" [abstract]. Arthritis Rheum. Sep. 2004; 59(9 Suppl):S336-S337. Abstract No. 804.
Kamatani, N. et al., "Phase II clinical trial using febuxostat (TMX-67), a novel-type xanthine oxidase/xanthine dehydrogenase inhibitor, for gout and hyperuricemia" in [Japanese] [abstract]. Gout and Nucleic Acid Metabolism. 2004; 28(1):38.
Kamatani, N. et al., "Phase II dose-response clinical trial using febuxostat (TMX-67), a novel-type xanthine oxidase/xanthine dehydrogenase inhibitor, for gout and hyperuricemia" [abstract]. Arthritis Rheum. Sep. 2003; 48(9 Suppl):S530. Abstract No. 1349.
Kang et al., Uric Acid and Chronic Renal Disease: Possible Implication of Hyperuricemia on Progression of Renal Disease, D. Kang T. Nakagawa, pp. 43-49, 2005.
Kelley et al., Effect of Allopurinol and Oxipurinol on Pyrimidine Synthesis in Cultured Human Fibroblasts, Biochemical Pharmacology, vol. 20, pp. 1471-1478, 1971.
Khosravan, R. et al., "Dose-related decreases in uric acid observed in a multiple-dose safety, pharmacokinetic, and pharmacodynamic study of TMX-67, a novel xanthine oxidase/dehydrogenase inhibitor, in healthy subjects" [abstract]. Arthritis Rheum. Sep. 2000; 43(9 Suppl):S401. Abstract No. 2009.
Khosravan, R. et al., Effect of concomitant administration of febuxostat and colchicine on pharmacokinetics of febuxostat and colchicine at steady state [abstract]. Arthritis Rheum. Sep. 2005; 52(9 Suppl):S102-S103. Abstract No. 188.
Khosravan, R. et al., "Effect of concomitant administration of febuxostat with naproxen or indomethacin on pharmacokinetics of febuxostat, naproxen, or indomethacin at steady state" [abstract]. Arthritis Rheum. Sep. 2005; 52(9 Suppl): S103. Abstract No. 189.
Khosravan R et al., Effect of febuxostat on pharmacokinetics and pharmacodynamics of warfarin [abstract].J Clin Pharmacol. Sep. 2005;45(9):1084. Abstract No. 71.
Khosravan, R. et al., "Effect of febuxostat on pharmacokinetics of desipramine, a CYP2D6 substrate, in healthy subjects" [abstract]. Clin Pharmacol Ther. Feb. 2005; 77(2):P43. Abstract No. PI-137.
Khosravan, R. et al., "Effect of food or antacid on febuxostat pharmacokinetics and pharmacodynamics in healthy subjects" [abstract]. Clin Pharmacol Ther. Feb. 2005; 77(2):P50. Abstract No. PI-161.
Khosravan, R. et al., "Effect of food or antacid on febuxostat pharmacokinetics and pharmacodynamics in healthy subjects" [abstract]. Pharmacotherapy Mar. 2006; 26:e24. Abstract No. 96E.
Khosravan, R. et al., "Effect of food or antacid on pharmacokinetics and pharmacodynamics of febuxostat in healthy subjects." Br J Clin Pharmacol (2007) 65(3):355-363.
Khosravan, R. et al., "Effect of mild and moderate hepatic impairment on pharmacokinetics, pharmacodynamics, and safety of febuxostat" [abstract]. J Clin Pharmacol. Sep. 2005; 45(9):1083. Abstract No. 69.
Khosravan, R. et al., "Effects of age and gender on febuxostat pharmacokinetics, pharmacodynamics, and safety in healthy subjects" [abstract]. Clin Pharmacol Ther. Feb. 2005; 77(2):P50. Abstract No. PI-162.
Khosravan, R. et al., "Febuxostat, a non-purine selective inhibitor of xanthine oxidase—effect of mild and moderate hepatic impairment on pharmacokinetics, pharmacodynamics, and safety" [abstract]. Arthritis Rheum. Sep. 2004; 50(9 Suppl):S337. Abstract No. 806.
Khosravan, R. et al., "Febuxostat, a novel non-purine selective inhibitor of xanthine oxidase—effect of renal impairment on pharmacokinetics, pharmacodynamics, and safety" [abstract]. J Clin Pharmacol. Oct. 2004; 44(10):1195. Abstract No. 45.

(56) References Cited

OTHER PUBLICATIONS

Khosravan, R. et al., "Pharmacokinetic interactions of concomitant administration of febuxostat and NSAIDs." J Clin Pharmacol. Aug. 2006; 46(8):855-866.

Khosravan, R. et al., "Pharmacokinetics, pharmacodynamics and safety of febuxostat, a non-purine selective inhibitor of xanthine oxidase, in a dose escalation study in healthy subjects." Clin Pharmacokinet. 2006;45(8):821-841.

Khosravan, R. et al., "Population pharmacokinetics and pharmacodynamics of febuxostat in a phase-II study of patients with gout" [abstract]. J Clin Pharmacol. Sep. 2005; 45(9):1083. Abstract No. 70.

Khosravan, R. et al., "Population pharmacokinetics and pharmacodynamics of febuxostat in a phase-III study of patients with gout" [abstract]. Clin Pharmacol Ther. Feb. 2006; 79(2):P21. Abstract No. PI-55.

Khosravan, R. et al., "The effect of age and gender on pharmacokinetics, pharmacodynamics, and safety of febuxostat, a novel nonpurine selective inhibitor of xanthine oxidase." J Clin Pharmacol. Sep. 2008; 48(9);1014-1024.

Khosravan, R. et al., "The effect of mild and moderate hepatic impairment on pharmacokinetics, pharmacodynamics, and safety of febuxostat, a novel nonpurine selective inhibitor of xanthine oxidase." J Clin Pharmacol. Jan. 2006; 46(1):88-102.

Komoriya, K. et al., Hypouricemic effect of allopurinol and the novel xanthine oxidase inhibitor TEI-6720 in chimpanzees. Eur J Pharmacol (1993) 250(3):455-460.

Komoriya, K. et al., Hypouricemic effect of a novel XOD inhibitor TEI-6720 in chimpanzees [in Japanese] [abstract]. Ryumachi. 1993;33:704.

Komoriya, K. et al., "Pharmacokinetics and pharmacodynamics of febuxostat (TMX-67), a non-purine selective inhibitor of xanthine oxidase/xanthine dehydrogenase (NPSIXO) in patients with gout and/or hyperuricemia." Nucleosides Nucleotides Nucleic Acids (2004) 23(8-9):1119-1122.

Kondo, S. et al., "Hypouricemic effects of TMX-67 (TE1-6720), a novel xanthine dehydrogenase/oxidase inhibitor, in rats and chimpanzees" [abstract]. Clin Biochem. Apr. 1997; 30(3):264. Abstract No. 90.

Krenitsky et al., Inhibition of Human Purine Nucleoside Phosphorylase, The Journal of Biological Chemistry, vol. 243, No. 11, pp. 2870-2881, 1968.

Krishnan et al., Long-term Cardiovascular Mortality Among Middle-aged Men with Gout, Arch Intern Med., vol. 168, No. 10, pp. 1104-1110, May 26, 2008.

Krishnan, Gout and Coronary Artery Disease—Epidemiologic Clues, Current Rheumatology Reports, vol. 10, pp. 249-255, 2008.

Kubo, J. et al., "Pharmacodynamics of TMX-67 (TE1-6720), a novel xanthine [sic] dehydrogenase/oxidase inhibitor, in man" [abstract]. Clin Biochem. (1997) 30(3):265. Abstract No. 93.

Kukulka, M. et al., "Effects of age and gender on febuxostat pharmacokinetics, pharmacodynamics, and safety in healthy subjects" [abstract]. Pharmacotherapy. Apr. 2006; 26(4):e23-e24. Abstract No. 95E.

Lawrence et al., Estimates of the Prevalence of Arthritis and Other Rheumatic Conditions in the United States, Arthritis & Rheumatism, Vo. 58, No. 1, pp. 26-35, Jan. 2008.

Lee et al., Allopurinol Hypersensitivity syndrome: A Preventable Severe Cutaneous Adverse Reaction, Singapore Med J., 49(5), pp. 384-387, 2008.

Lee et al., Serum uric Acid is Associated with Microalbuminura in Prehypertension, Hypertension, vol. 47, pp. 962-967, 2006.

Lehto et al., Serum Uric Acid is a Strong Predictor of Stroke in Patients with Non-Insulin-Dependent Diabetes Mellitus, American Heart Association, pp. 635-639, 1998.

Liu-Bryan et al., "Evil humors take their toll as innate immunity makes gouty joints TREM-ble," Arthritis & Rheum. Feb. 2006; 54(2):383-386.

Li-Yu et al., Treatment of Chronic Gout. Can we Determine when Urate Stores are Depleted Enough to Prevent Attacks of Gout?, The Journal of Rheumatology, 28:3, pp. 557-580, 2001.

Lonjou et al., A European study of HLA-B in Stevens-Johnson syndrome and toxic epidermal necrolysis related to five high-risk drugs, Pharmacogenetics and Genomics, vol. 18, No. 2, pp. 99-107, 2008.

MacDonald, P.A. et al., "Febuxostat versus allopurinol versus placebo in the treatment of gout in African-American subjects" [abstract]. J Natl Med Assoc. Aug. 2006; 98(8):1389-1390.

MacDonald, P.A. et al., "Febuxostat vs. allopurinol and placebo in subjects with hyperuricemia and gout: the 28-week APEX study" [abstract]. Pharmacotherapy Oct. 2006; 26(10):e94. Abstract No. 267E.

Manfredi, R.L. et al., "Inhibition of theophylline metabolism by long-term allopurinol administration," Clin. Pharmacol. Ther. (1981) 29(2):224-229.

Mayer, M.D. et al., "Pharmacokinetics and pharmacodynamics of febuxostat, a new non-purine selective inhibitor of xanthine oxidase in subjects with renal impairment." Am J Ther. Jan.-Feb. 2005; 12(1):22-34.

Mazzali, M. et al., "Elevated uric acid increases blood pressure in the rat by a novel crystal-independent mechanism." Hypertension (2001) 38:1101-1106.

Mazzali et al., Hyperuricemia induces a primary arteriolopathy in rats by a blood pressure-independent mechanism, Am J Physiol Renal Physiol, 282, pp. F991-F997, 2002.

McDonald, P.A., et al., "Febuxostat versus allopurinol controlled trial in subjects with hyperuricemia and gout (FACT): a multicenter, phase 3, randomized, controlled, double-blind clinical study" [abstract]. Consult Pharm. Jan. 2006; 21(1):77.

McKendrick et al., Allopurinol hypersensitivity, British Medical Journal, p. 998, Apr. 14, 1979.

Melethil, S. et al., "Steady state urinary excetion of theophylline and its metabolites in the presence of erythromycin." Res. Commun Chem. Pathol. Pharmacol. (1982) 35(2):341-344.

Merck Manual, The, 17th edition (Japanese version), Nikkei Business Publications, Inc. (1999) 464-468.

Miyamoto, Y. et al., "Potentiation of Nitric Oxide-Mediated Vasorelaxation by Xanthine Oxidase Inhibitors (43982)", NO-Mediated Vasorelaxation, Proceedings of the Society for Experimental Biology and Medicine (1996) 211(4):366-373.

Mochizuki, H. et al., "Polymorphism studies of TEI-6720" [abstract]. AAPS PharmSci. 2001;3(S1).

Mockenhaupt et al., Stevens-Johnson Syndrome and Toxic Epidermal Necrolysis: Assessment of Medication Risks with Emphasis on Recently Marked Drugs. The EuroSCAR-Study, Journal of Investigative Dermatology, vol. 128, pp. 35-44, 2008.

Moriwaki, Y., et al. Study on crystal polymorphism of TEI-6720 [in Japanese] [abstract]. Journal of Pharmaceutical Science and Technology, Japan. 2002;62(Suppl):279.

Mukoyoshi, M. et al., "In vitro drug-drug interaction studies with febuxostat, a novel non-purine selective inhibitor of xanthine oxidase: plasma protein binding, identification of metabolic enzymes and cytochrome P450 inhibition," Xenobiotica (2008) 38(5):496-510.

Nakagawa et al., Uric Acid—A Uremic Toxin, Blood Purif, 24, pp. 67-70, 2006.

Nakagawa, T. et al., "A casual role for uric acid in fructose-induced metabolic syndrome," Am. J. Physiol. Renal Physiol. (2006) 290:F625-631.

National Kidney Foundation, "Definition and Classification of Stages of Chronic Kidney Disease," American Journal of Kidney Diseases, vol. 39, No. 2, Suppl 1, pp. S46-S75, Feb. 2002.

National Kidney Foundation, "What you need to know about urinalysis," (2002) 1-10.

Newaz, M.A. et al., "Uric acid, xanthane oxidase and other risk factors of hypertension in noormotensive subjectives," CAS accession #1996:571720, Clinical and experimental hypertension (1996) 18:1035-1050.

Ochiai et al., Uric Acid Renal Excretion and Renal Insufficiency in Decompensated Severe Heart Failure, The European Journal of Heart Failure 7, pp. 468-474, 2005.

(56) References Cited

OTHER PUBLICATIONS

Okamoto et al., An Extremely Potent Inhibitor of Xanthine Oxidoreductase, Crystal Structure of the Enzyme-Inhibitor Complex and Mechanism of Inhibition, The Journal of Biological Chemistry, vol. 278, No. 3, pp. 1848-1855 (2003).

Osada, Y. et al., "Hypouricemic effect of the novel xanthine oxidase inhibitor, TEI-6720, in rodents." Eur J Pharmacol (1993) 241(2/3):183-188.

Ouyang et al., Fructose Consumption as a risk factor for Non-Alcoholic fatty liver disease, Journal of Hepatology, vol. 48, pp. 993-999, 2008.

Pacher et al., Pharm Rev. (2006) 58:87-114.

Padang et al., Characteristics of Chronic Gout in Northern Sulawesi, Indonesia, The Journal of Rheumatology, 33:9, pp. 1813-1817, 2006.

Patetsios et al., Identification of Uric Acid and Xanthine Oxidase in Atherosclerotic Plaque, The American Journal of Cardiology, vol. 88, pp. 188-191, Jul. 15, 2001.

Peres-Ruiz et al., Using Serum Urate Levels to Determine the Period Free of Gouty Symptoms after withdrawal of long-term Urate-Lowering Therapy: A Prospective Study, Arthritis & Rheumatism, vol. 55, No. 5, pp. 786-790, Oct. 15, 2006.

Perez-Ruiz et al., Renal Underexcretion of Uric Acid Is Present in Patients with Apparent High Urinary Uric Acid Output, Arthritis & Rheumatism, vol. 47, No. 6, pp. 610-613, Dec. 15, 2002.

Perez-Ruiz, F. et al., "Effect of urate-lowering therapy on the velocity of size reduction of tophi in chronic gout," Arthr. Rheum. (2002) 47(4):356-360.

Perlstein et al., Uric Acid and the State of Intrarenal renin-angiotensin system in humans, Kidney International, vol. 66, pp. 1465-1470, 2004.

Petersel et al. Treatment of Acute Gout in Hospitalized Patients, The Journal of Rheumatology, 34:7, pp. 1556-1568, 2007.

Pharmaprojects: PHAR PHLP PHDI (PHZZ), BOF-4272, PJB Publications, Ltd, Richmond, UK, (1998) 2 pages.

R&D Insight, BOF 4272, Adis International, 2003, 3 pages.

R&D Insight, Research programme, Adis International Ltd., 2003, 2 pages.

Reinders et al., Biochemical effectiveness of allopurinol and allopurinol-probenecid in Previously Benzbromarone-treated gout Patients, Clin Rheumatol, 26, pp. 1459-1465,2007.

Reyes, The Increase in Serum Uric Acid Concentration caused by diuretics might be beneficial in heart failure, The European Journal of Heart Failure, vol. 7, pp. 461-467, 2005.

Robert, Predictability of creatinine Clearance estimates in critically ill patients, Critical Care Medicine, vol. 21, No. 10, pp. 1487-1495, 1993.

Rosenberg, "Skeletal system and soft tissue tumors," Pathologic Basis of Disease, Chapter 27, 5th Edition, pp. 1213-1271.

Sanchez-Lozada, L.G. et al., "Effects of febuxostat on metabolic and renal alterations in rats with fructose-induced metabolic syndrome." Am J Physiol Renal Physiol. 2008 294:F710-F718.

Sanchez-Lozada, L.G. et al., Treatment with the xanthine oxidase inhibitor febuxostat lowers uric acid and alleviates systemic and glomerular hypertension in experimental hyperuricaemia. Nephrol Dial Transplant. (2008) 23:1179-1185.

Sanchez-Lozada, L.G. et al., "Effect of febuxostat on the progression of renal disease in 5/6 nephrectomy rats with and without hyperuricemia." Nephron Physiol (2008) 108:p. 69-p. 78.

Sanchez-Lozada, L.G. et al., "Effect of febuxostat on the progression of renal disease in 5/6 Nx rats with and without hyperuricemia" [abstract]. J Am Soc Nephrol. Oct. 2007; 18:400A. Abstract No. SA-PO262.

Sarawate et al., "Serum Urate Levels and Gout Flares Analysis From Managed Care Data," Journal of Clinical Rheumatology, vol. 12, No. 2, pp. 61-65, Apr. 2006.

Sarawate et al., Gout medication Treatment Patterns and Adherence to Standards of Care from a managed Care Perspective, Mayo Clin Proc. vol. 81(7), pp. 925-934, Jul. 2006.

Sato, S. et al. "A Novel Xanthine Dehydrogenase Inhibitor (BOF-4272)," Purine and Pyrimidine Metabolism in Man, ed. By R.A. Harkness, Plenum Press, NY (1991) VII, Part A, 135-138.

Schlesinger et al., Gout Can management be improved?, Current Opinion in Rheumatology, vol. 13, pp. 240-244, 2001.

Schlesinger et al., Update on Gout, Arthritis & Rheumatism, vol. 47, No. 5, pp. 563-565, Oct. 15, 2002.

Schumacher, H.R. et al., "A phase 2, long term open-label safety and efficacy study of febuxostat, a novel non-purine, selective inhibitor of xanthine oxidase" [abstract]. Arthritis Rheum. Sep. 2004; 50(9 Suppl):5335. Abstract No. 800.

Schumacher, H.R. et al., "Direct physical measurement method for evaluation of tophus nodules in subjects with gout" [abstract]. Arthritis Rheum. Sep. 2003; 48(9 Suppl):S637-S638. Abstract No. 1664.

Schumacher, H.R. et al., "Febuxostat vs. allopurinol and placebo in subjects with hyperuricemia and gout: the 28-week APEX study" [abstract]. Arthritis Rheum. Sep. 2005; 52(9 Suppl):S680. Abstract No. 1837.

Schumacher, H.R. et al., "Long-term safety and efficacy of febuxostat, a novel non-purine selective inhibitor of xanthine oxidase, in subjects with hyperuricemia and gout" [abstract]. Ann Rheum Dis. Jul. 2005; 64(Suppl 3):498. Abstract No. SAT0282.

Schumacher, H.R. et al., "Magnetic resonance imaging of gouty tophi during treatment with febuxostat, a non-purine selective inhibitor of xanthine oxidase" [abstract]. Arthritis Rheum. Sep. 2004; 50(9 Suppl):S336. Abstract No. 802.

Schumacher, H.R. Jr, et al., Effects of febuxostat versus allopurinol and placebo in reducing serum urate in subjects with hyperuricemia and gout: A 28-week, phase III, randomized, double-blind, parallel-group trial. Arthritis Care Res. Nov. 2008; 59(11):1540-1548.

Schumacher, H.R. Jr, et al., "Febuxostat (FEB) versus Allopurinol (ALLO) in the Treatment of Gout in Subjects >= 65 Years of Age" [abstract]. J Am Geriatr Soc. Apr. 2008; 56(s1):5126. Abstract No. C44.

Schumacher, H.R. Jr, et al., "Febuxostat in the treatment of gout: 5-yr findings of the FOCUS efficacy and safety study." Rheumatology (2009) 48(2):188-194.

Schumacher, H.R. Jr, et al., "Febuxostat versus allopurinol in the treatment of gout in subjects 65 years of age or older" [abstract]. Ann Rheum Dis. Jul. 2007; 66(Suppl II):234-235. Abstract No. THU0353.

Schumacher, H.R. Jr, et al., "Long-term efficacy and safety of febuxostat (FEB) in patients with gout: results of the five-year FOCUS study" [abstract]. J Clin Rheumatol. Aug. 2008; 14(4):S4.

Schumacher, H.R. Jr, et al., "Magnetic resonance imaging in the quantitative assessment of gouty tophi" [erratum in: Int J Clin Pract May 2006; 60(5):630]. Int J Clin Pract. Apr. 2006; 60(4):408-414.

Schumacher, H.R. Jr, et al., "Phase 2, long-term, open-label safety and efficacy study of febuxostat, a novel nonpurine, selective inhibitor of xanthine oxidase" [abstract]. J Natl Med Assoc. Jun. 2005; 97(6):901.

Schumacher, H.R. Jr, et al., "Reduction in gout flares and tophus size in the 52-week Febuxostat Allopurinol controlled trial (FACT)" [abstract]. J Clin Rheumatol. Aug. 2006; 12(4 Suppl): S9. Abstract No. 28.

Schumacher, H.R., et al., "The focus trial 48-month interim analysis: long-term clinical outcomes of treatment with febuxostat in subjects with gout in an ongoing phase 2, open-label extension study" [abstract]. Ann Rheum Dis. Jul. 2006; 65(Suppl 2):93. Abstract No. OP0130.

Schumacher, H.R. Jr, et al., "The FOCUS trial 48-month interim analysis: long-term clinical outcomes of treatment with febuxostat in subjects with gout in an ongoing phase 2, open-label extension study" [abstract]. Arthritis Rheum. Sep. 2006; 54(9 Suppl):S319-S320. Abstract No. 703.

Schumacher, H.R. Jr, et al., "Tophaceous gout: quantitative evaluation by direct physical measurement." J Rheumatol. Dec. 2005; 32(12):2368-2372.

Shoji et al., A Retrospective Study of the Relationship Between Serum Urate Level and Recurrent Attacks of Gouty Arthritis: Evidence for Reduction of Recurrent Gouty Arthritis with Antihyperuricemic Therapy, Arthritis & Rheumatism, vol. 51, No. 3, pp. 321-325, Jun. 15, 2004.

(56) References Cited

OTHER PUBLICATIONS

Siu, Y. et al., "Use of allopurinol in slowing the progression of renal disease through its ability to lower serum uric acid level." American Journal of Kidney Diseases (2006) 47(1):51-59.

Sturm et al., Uric Acid as a risk factor for progression of non-diabetic chronic kidney disease? The mild to Moderate Kidney Disease (MMKD) Study, Experimental Gerontology, vol. 43, pp. 347-352, 2008.

Suliman et al., J-Shaped Mortality Relationship for Uric Acid in CKD, American Journal of Kidney Diseases, vol. 48, No. 5, pp. 761-771, Nov. 2006.

Suzuki, H. et al., "Xanthine oxidase activity associated with arterial blood pressure in spontaneously hypertensive rats." Proc Natl. Acad. Sci. USA, Apr. 1998; 95(8):4754-4759.

Swan, S., et al., "Effect of renal impairment on pharmacokinetics, pharmacodynamics, and safety of febuxostat (TMX-67), a novel non-purine selective inhibitor of xanthine oxidase" [abstract]. Arthritis Rheum. Sep. 2003; 48(9 Suppl):S529. Abstract No. 1348.

Takano, Y. et al. "Selectivity of febuxostat, a novel non-purine inhibitor of xanthine oxidase/xanthine dehydrogenase," Life Sciences (2005) 76(16):1835-1847.

Talaat et al., The Effect of Mild Hyperuricemia on Urinary Transforming Growth Factor Beta and the Progression of Chronic Kidney Disease, American Journal of Nephrology, vol. 27, pp. 435-440, 2007.

Tausche, A-K et al., "The Janus Faces of Allopurinol—Allopurinol Hypersensitivity Syndrome," The American Journal of Medicine, vol. 121, No. 3, pp. e3-e4, Mar. 2008.

Terkeltaub et al., Recent developments in our understanding of the renal basis of hyperuricemia and the Development of Novel Antihyperuricemic Therapeutics, Arthritis Research & Therapy, vol. 8 (Suppl 1), pp. 1-9, 2006.

Terkeltaub, "Gout in 2006. The perfect storm," Bulletin of the NYU Hospital for Joint Diseases, vol. 64, No. 1 & 2, pp. 82-86, 2006.

Terkeltaub, "Gout," The New England Journal of Medicine, 349:17, pp. 1647-1655, Oct. 23, 2003.

Terkeltaub, "Pathogenesis and treatment of crystal-induced inflammation," in Arthritis and Allied Conditions, A Textbook of Rheumatology, vol. 2, pp. 2329-2347, 2001.

Thomson Current Drugs, Patent Report for WO-03064410 (2003) 1 page.

Uematsu, T. et al., "Pharmacokinetic and Pharmacodynamic Properties of a Novel Xanthine Oxidase Inhibitor, BOF-4272, in Healthy Volunteers," J. Pharm. Exp. Ther. (1994) 270(2):453-459.

Wallace et al., Preliminary Criteria for the Classification of the Acute Arthritis of Primary Gout, Arthritis and Rheumatology, vol. 20, No. 3, pp. 895-900, Apr. 1977.

Wallace et al., Therapy in Gout, Rheumatic Disease Clinics of North America, vol. n14, No. 2, pp. 441-457, Aug. 1988.

Website pages from www.marvistavent.com, regarding Carprofen, Brand Name: Rimadyl, Jul. 24, 2006.

Whelton, A. et al., "Beneficial relationship of serum urate (sUA) reduction and estimated glomerular filtration Rate (eGFR) improvement/maintenance in hyperuricemic gout subjects treated for up to 5.5 years with febuxostat (FEB)" [abstract]. Arthritis Rheum. Dec. 2008; 58(12):3975. Abstract No. L7.

Whelton, A. et al., "Febuxostat, a novel non-purine selective inhibitor of xanthine oxidase, in patients with a history of nephrolithiasis" [abstract]. J Am Soc Nephrol. (2006) 17:525A. Abstract No. F-PO894.

Whelton, A. et al., "Patients with gout and a history of nephrolithiasis, treated with febuxostat, a novel non-purine selective inhibitor of xanthine oxidase, for more than 5 Years" [abstract]. Ann Rheum Dis. Jul. 2007; 66(Suppl II):624. Abstract No. AB0749.

Worcester, E.M. et al., "Renal function in patients with nephrolithiasis," J. Urology (2006) 176(2):600-603.

Wortmann, R. et al., "Gout flare prophylaxis during management of chronic gout with febuxostat, a non-purine selective inhibitor of xanthine oxidase" [abstract]. Arthritis Rheum. Sep. 2004; 50(9 Suppl):S335-S336. Abstract No. 801.

Wortmann, RL et al., "Effect of febuxostat or allopurinol on the clinical manifestations of gout: reduction in gout flares and tophus size over time in the EXCEL trial" [abstract]. Arthritis Rheum. Sep. 2006; 54(9 Suppl):S642. Abstract No. 1592.

Wortmann, R.L. et al., "Gout flare prophylaxis during management of chronic gout with febuxostat, a nonpurine selective inhibitor of xanthine oxidase" [abstract]. J Natl Med Assoc. Jun. 2005; 97(6):895-896.

Wortmann, R.L. et al., "Reduction in tophus size in subjects with chronic gout treated with febuxostat or allopurinol for 52 weeks—FACT trial" [abstract]. Arthritis Rheum. Sep. 2005; 52(9 Suppl):S108. Abstract No. 203.

Wortmann, Gout and Other Disorders of Purine Metabolism, pp. 2158-2166, Chapter 344.

Wortmann, R.L. "Recent advances in the management of gout and hyperuricemia," Current Opinion in Rheumatology (2005) 17(3):319-324.

Xanthine oxidase inhibitors, Yamasa Shyoyu, Drug Print Report, http://release2.i.../reports.print_display?i_query_id=1214721 &template=DrugPrint&id=1093, Jan. 17, 2003, 2 pages.

Xu, X. et al., "Xanthine Oxidase Inhibition with Febuxostat Attenuates Systolic Overload-Induced Left Ventricular Hypertrophy and Dysfunction in Mice." J Cardiac Fail (2008) 14(9):746-753.

Xu, X. et al., "Delayed Treatment Effects of Xanthine Oxidase Inhibition on Systolic Overload-Induced Left Ventricular Hypertrophy and Dysfunction," Takeda Global Research & Development Center, Inc., Deerfield, IL. Presented at the 13th International Symposium on Purine and Pyrimidine Metabolism in Man, Stockholm, Sweden, Jun. 21-24, 2009. Nucleosides Nucleotides and Nucleic Acids (2010) 29:306-313.

Yamaguchi, S., "Treatment for hyperuricosemia in patients with urolithiasis including uric acid stone," Progress in Medicine (2004) 24(5):1213-1218 (Japanese Publication).

Yamamoto, T. et al., Effect of TEI-6720, a xanthine oxidase inhibitor, on the nucleoside transport in the lung cancer cell line A549. Pharmacology 2000 60:34-40.

Yonezawa, H. et al., "Pharmacokinetics of TMX-67 (TEI-6720), a novel xanthine dehydrogenase/oxidase inhibitor, in man" [abstract]. Clin Biochem. Apr. 1997; 30(3):296-297. Abstract No. 221.

Yu, P. et al., "Effect of febuxostat, a novel non-purine, selective inhibitor of xanthine oxidase, on the QT interval in healthy subjects" [abstract]. J Clin Pharmacol. Oct. 2004; 44(10):1195. Abstract No. 46.

Zhang, W., "EULAR evidence based recommendations for gout. Part 1: Diagnosis. Report of a Task Force of the Standing Committee for International Clinical Studies including Therapeutics (ESCISIT),", Ann Rheum Dis 2006; 65, pp. 1301-1311.

Zhao, L. et al., "Chronic xanthine oxidase inhibition following myocardial infarction in rabbits: effects of early versus delayed treatment." Life Sci. (2008) 82:495-502.

Zhao L et al., Effect of febuxostat, a novel non-purine, selective inhibitor of xanthine oxidase (NP-SIXO), on enzymes in purine and pyrimidine metabolism [abstract]. Arthritis Rheum. Sep. 2003;48(9 Suppl): S531. Abstract No. 1352.

Zhao, L. et al., "Febuxostat, a non-purine selective inhibitor of xanthine oxidase, has a voltage-dependent agonist effect on hERG potassium currents" [abstract]. Heart Rhythm. May 2006; 3(5 Suppl):S261. Abstract No. P5-4.

United States Patent Office Action for U.S. Appl. No. 11/939,112 dated Oct. 27, 2011 (18 pages).

United States Patent Office Action for U.S. Appl. No. 11/939,112 dated Feb. 1, 2011 (12 pages).

United States Patent Office Action for U.S. Appl. No. 12/015,527 dated Aug. 17, 2011 (14 pages).

United States Patent Office Action for U.S. Appl. No. 12/015,527 dated Nov. 9, 2010 (10 pages).

United States Patent Office Action for U.S. Appl. No. 11/497,608 dated Mar. 27, 2012 (26 pages).

United States Patent Office Action for U.S. Appl. No. 11/497,608 dated Apr. 29, 2009 (10 pages).

United States Patent Office Action for U.S. Appl. No. 11/497,608 dated Sep. 12, 2008 (16 pages).

(56) References Cited

OTHER PUBLICATIONS

United States Patent Office Action for U.S. Appl. No. 11/497,608 dated Nov. 15, 2007 (9 pages).
United States Patent Office Action for U.S. Appl. No. 12/689,266 dated Mar. 15, 2012 (20 pages).
United States Patent Office Action for U.S. Appl. No. 12/210,207 dated Sep. 27, 2011 (19 pages).
United States Patent Office Action for U.S. Appl. No. 12/210,207 dated Feb. 7, 2011 (12 pages).
United States Patent Office Action for U.S. Appl. No. 13/295,696 dated Apr. 12, 2012 (10 pages).
International Search Report and Written Opinion for Application No. PCT/US2011/050870 dated Nov. 29, 2011 (14 pages).
International Search Report and Written Opinion from PCT/US08/51248 mailed Jun. 25, 2008 (12 pages).
International Search Report and Written Opinion from PCT/US06/30023 mailed Dec. 7, 2007 (11 pages).
International Search Report and Written Opinion from PCT/US07/84573 mailed Apr. 25, 2008 (8 pages).
International Search Report and Written Opinion from PCT/US06/17663 mailed Nov. 27, 2006 (4 pages).
International Search Report from PCT/US2007/084573 dated Feb. 25, 2008 (6 pages).
European Search Report and Opinion from Application No. 07864338.4 mailed Dec. 29, 2009 (7 pages).
European Search Report and Opinion from Application No. 06759284 mailed Dec. 29, 2009 (12 pages).
Supplementary European Search Report and Opinion from Application No. 07864338.4 mailed Nov. 4, 2009 (13 pages).
Supplementary European Search Report and Opinion from Application No. 08705967 dated Dec. 22, 2009 (7 pages).
European Patent Office Action for Application No. 07864338.4 dated Jan. 14, 2011 (7 pages).
Schneider, HJ, et al., "Prevention of recurrent uric acid and calcium oxalate stones by administration of the xanthine oxidase inhibitors Milurit 100 and Milurit 300," International Urology and Nephrology, 1983;15(2):121-9.
Beer, MH, et al., "Urinary calculi," in The Merck Manual, Merck, NJ, USA, pp. 1838-1840.
Sorbera, LA, et al., "TMX-67: Treatment of gout and hyperuricemia, xanthine oxidase inhibitor: TEI-6720," Drugs of the Future, 2001;26(1):32-8.
Beer, MH, et al., The Merck Manual, 1999, Merck, NJ, USA, pp. 460-464.
Hartung, R, "Nephrolithiasis in hyperuricemia and gout," Aktuelle Endokrinologie und Stoffwechsel, 1982;3 (4):164-7.
Supplementary European Search Report for EP1883405 mailed Feb. 16, 2010.
Supplementary European Search Report for EP1883405 dated Oct. 30, 2009.
European Search Report and Opinion from EP Application No. 06759284 (EP1883405) mailed Dec. 29, 2009.
United States Patent Office Action for U.S. Appl. No. 12/210,207 dated Jul. 31, 2012 (18 pages).

Brennan, M.R. et al., "Comparing rates of dyspepsia with coxibs vs. NSAIDPPI: a meta-analysis," The Amer. J. of Med. (2006) 119:448. e27-448.e36.
Edwards, N.L., "Febuxostat: a new treatment for hyperuricaemia in gout," Rheumatology (2009) 48:ii15-ii19.
Schumacher, H.R., Jr., "The pathogenesis of gout," Cleveland Clin. J. Med. (2008) 75(5):S2-S4.
Zhang, W. et al., "EULAR evidence based recommendations for gout. Part II: Management. Report of a task force of the EULAR Standing Committee for International Clinical Studies Including Therapeutics (ESCISIT)," Ann. Rheum. Dis. (2006) 65:1312-1324.
United States Patent Office Action for U.S. Appl. No. 13/521,765 mailed Feb. 18, 2014 (13 pages).
Ernst, M.E. et al., "Febuxostat: a selective xanthine-oxidase/xanthine-dehydrogenase inhibitor for the management of hyperuricemia in adults with gout," Clin. Therap. (2009) 31(11):2503-2518.
Erokhin, A.P. etal., "Cryptorchidism," Moscow (1995) p. 209, Chapter 5, English translation.
Puig, J.G. et al., "Inhibition of xanthine oxidase by allopurinol: a therapeutic option for ischaemia induced pathological processes," Annals of Rheumatic Diseases (1989) 883-888.
Svetkey, L.P., "Management of prehypertension," Hypertension (2005) 45:1056-1061.
Takao, S., "Hypertension—its pathological condition and treatment (1) hypertension treatment and guidelines," Medicine and Pharmacy (2003) 50(5):588-594.
Tareeva, I.E., Nephrology. Guide for Physicians. 2nd Edition, Moscow: Meditsina (2000) 422-428.
Traynor, K., "New gout treatment approved," Amer. J. Health-Syst. Pharm. (2009) 66:606-607.
United States Patent Office Action for U.S. Appl. No. 12/015,527 dated Nov. 1, 2013.
United States Patent Office Action for U.S. Appl. No. 12/689,266 dated Oct. 26, 2012 (11 pages).
United States Patent Office Action for U.S. Appl. No. 13/227,828 dated Jul. 18, 2013 (13 pages).
United States Patent Office Action for U.S. Appl. No. 13/295,696 dated Nov. 6, 2012 (12 pages).
United States Patent Office Notice of Allowance for U.S. Appl. No. 13/295,696 dated Dec. 4, 2012 (8 pages).
International Search Report for Application No. PCT/US2011/025450 dated May 2, 2011 (2 pages).
Written Opinion for Application No. PCT/US2011/025450 dated May 2, 2011 (6 pages).
"Uloric (febuxostat) tablet for oral use" label, Feb. 13, 2009, 17 pages.
U.S. FDA approval letter of uloric to Takeda Pharmaceuticals North America, Inc., NDA 21-856, dated Feb. 13, 2009, 6 pages.
United States Patent Office Action for U.S. Appl. No. 13/227,828 dated Nov. 15, 2013 (7 pages).
Reagan-Shaw et al., "Dose translation from animal to human studies revisited," FASEB Journal (2008) 22:659-661.
Response to European Search Report for Application No. 11796331.4 dated Jun. 6, 2014.
Notice of Allowance for U.S. Appl. No. 13/227,828 dated May 29, 2014 (9 pages).

* cited by examiner

METHODS FOR TREATING NEPHROLITHIASIS

This application claims priority to U.S. Application No. 60/678,987 filed on May 9, 2005, the contents of which are herein incorporated by reference.

FIELD OF THE INVENTION

The present invention relates to methods of treating subjects suffering from nephrolithiasis. More specifically, the present invention involves administering to a subject in need of treatment thereof a therapeutically effective amount of at least one xanthine oxidoreductase inhibiting compound or salt thereof.

BACKGROUND OF THE INVENTION

Nephrolithiasis is a condition in which one or more calculi (stones) are present in the kidneys. In addition to being present in the kidneys, these stones can also travel into the ureter (which is referred to as ureterolithiasis). Stone formation results when urine becomes supersaturated with certain poorly soluble stone-forming constituents, such as calcium, uric acid, etc. The chemical composition of a stone depends on the stone-forming constituents present in the urine. The four most common types of stones are calcium stones, uric acid stones, cystine stones and struvite stones. Calcium stones are the most common type of stones. Several different types of calcium stones are known, such as calcium oxalate stones, calcium phosphate stones and calcium oxalate and phosphate stones. Calcium stones develop as a result of hypercalciuria, metabolic or hormonal disorders (such as hyperparathyroidism and rental tubular acidosis), etc. Uric acid stones can develop as a result of a diet high in purines. Moreover, conditions such as gout and treatments such as chemotherapy can also increase the risk of uric acid stones. Cystine stones form as a result of a rare, congenital condition known as cystinuria that results in large amounts of cystine being present in the urine. Struvite stones develop when a urinary tract infection (i.e. cystitis) affects the chemical balance of the urine.

In the kidney, stones grow on the surfaces of the papillae, detach and accompany urine as it travels out of the kidney and into the ureter. Kidney stones that are very small (i.e., under four millimeters), are capable of moving through the urinary tract without any symptoms. Such stones are referred to as "silent" stones. However, larger stones, cannot be excreted and even smaller stones can become lodged in the ureter. When a stone becomes lodged in the urinary tract, it can cause irritation or blockages. When such lodging or blockage occurs, the stones cause the urinary tract to go into a spasm, a condition known as "renal colic". Renal colic causes a severe cramping pain felt in the back and side and, sometimes, in the lower abdomen. Eventually, pain may spread to the groin. Irritation of the urinary tract often causes frequent urination. Blockages can also result in difficulty urinating. Blood in the urine, also called hematuria, is also common. In addition to renal colic, hematuria and frequent urinating, other symptoms of kidney stones include nausea, vomiting, a burning sensation while urinating, fever and/or chills.

Unfortunately, about fifteen (15) percent of men and about seven (7) percent of women will experience at least one kidney stone by age 70. In fact, kidney stones affect about 2 out of every 1,000 people per year. Recurrence is common, and the risk of recurrence is greater if two or more episodes of kidney stones have occurred. A number of drugs are used for treating patients suffering from recurring nephrolithiasis, such as thiazides (i.e. hydrochlorothiazide), potassium citrate and allopurinol (Allopurinol is well known in the art as a non-selective xanthine oxidase inhibitor that is commonly prescribed for treating gout. Allopurinol is a purine analogue and as such, its structure is similar to purines. However, allopurinol is known to inhibit a number of enzymes involved in purine/pyrimidine metabolism, such as purine nucleoside phosphorylase and orotidine-5'-monophosphate decarboxylate). The kind of drugs selected for treatment depends on the composition of the stones and on the underlying condition which caused the stone formation. However, each of these drugs causes a number of side effects. For example, the major side effect associated with thiazides is hypokalemia, which leads to reductions in urinary citrate excretion. Some patients that receive potassium citrate therapy experience gastrointestinal intolerance, especially older patients and patients with dyspepsia. Side effects caused by allopurinol include, but are not limited to, rash, hypertension, blood disorders, gastrointestinal disorders, etc. Therefore, there is a need in the art for new and improved therapeutic agents that can be used in treating patients suffering from nephrolithiasis.

SUMMARY OF THE PRESENT INVENTION

In one embodiment, the present invention relates to a method for treating nephrolithiasis in a subject in need of treatment thereof. The method involves the step of administering to the subject a therapeutically effective amount of at least one compound, wherein said at least one compound is a xanthine oxidoreductase inhibitor or a pharmaceutically acceptable salt thereof. Examples of xanthine oxidoreductase inhibitors that can be used in the above-described method include, but are not limited to, 2-[3-cyano-4-(2-methylpropoxy)phenyl]-4-methylthiazole-5-carboxylic acid, 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid, 1-(3-cyano-4-(2,2-dimethylpropoxy)phenyl)-1H-pyrazole-4-carboxylic acid or pharmaceutically acceptable salts thereof.

In yet another embodiment, the present invention relates to a method for reducing the number of incidence of kidney stone attacks in a subject having a history of nephrolithiasis. The method involves the step of administering to the subject a therapeutically effective amount of at least one compound, wherein said at least one compound is a xanthine oxidoreductase inhibitor or a pharmaceutically acceptable salt thereof. Examples of xanthine oxidoreductase inhibitors that can be used in the above-described method include, but are not limited to, 2-[3-cyano-4-(2-methylpropoxy)phenyl]-4-methylthiazole-5-carboxylic acid, 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid, 1-(3-cyano-4-(2,2-dimethylpropoxy)phenyl)-1H-pyrazole-4-carboxylic acid or pharmaceutically acceptable salts thereof.

In yet still another further embodiment, the present invention relates to a method of reducing the number of incidence of kidney stone attacks in a subject suffering from hyperuricemia. The method involves the step of administering to the subject a therapeutically effective amount of at least one compound, wherein said at least one compound is a xanthine oxidoreductase inhibitor or a pharmaceutically acceptable salt thereof. Examples of xanthine oxidoreductase inhibitors that can be used in the above-described method include, but are not limited to, 2-[3-cyano-4-(2-methylpropoxy)phenyl]-4-methylthiazole-5-carboxylic acid, 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid, 1-(3-cyano-4-(2,2-dimethylpropoxy)phenyl)-1H-pyrazole-4-carboxylic acid or pharmaceutically acceptable salts thereof.

In yet another embodiment, the present invention relates to a method for preventing kidney stone attacks in a subject having a history of nephrolithiasis. The method involves the step of administering to the subject a prophylactically effective amount of at least one compound, wherein said at least one compound is a xanthine oxidoreductase inhibitor or a pharmaceutically acceptable salt thereof. Examples of xanthine oxidoreductase inhibitors that can be used in the above-described method include, but are not limited to, 2-[3-cyano-4-(2-methylpropoxy)phenyl]-4-methylthiazole-5-carboxylic acid, 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid, 1-(3-cyano-4-(2,2-dimethylpropoxy)phenyl)-1H-pyrazole-4-carboxylic acid or pharmaceutically acceptable salts thereof.

In still another embodiment, the present invention relates to a method for treating nephrolithiasis in a subject in need of treatment thereof. The method involves the step of administering to the subject a therapeutically effective amount of at least one compound, wherein said at least one compound has the following formula:

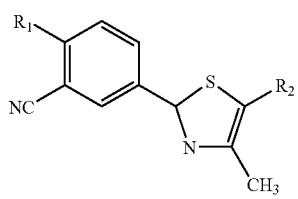

wherein $R_1$ is a hydroxyl group, an unsubstituted or substituted $C_1$-$C_{10}$ alkoxy or an unsubstituted or substituted hydroxyalkoxy; and $R_2$ is COOH, COO-Glucoronide or COO-Sulfate.

Examples of compounds having the above-identified formula that can be used in this method include, but are not limited to, 2-[3-cyano-4-(2-methylpropoxy)phenyl]-4-methylthiazole-5-carboxylic acid, 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid or pharmaceutically acceptable salts thereof.

In yet another embodiment, the present invention relates to a method for reducing the number of incidence of kidney stone attacks in a subject having a history of nephrolithiasis. The method involves the step of administering to the subject a therapeutically effective amount of at least one compound, wherein said at least one compound has the following formula:

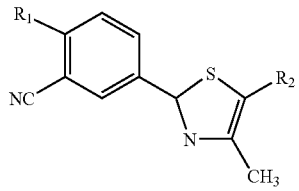

wherein $R_1$ is a hydroxyl group, an unsubstituted or substituted $C_1$-$C_{10}$ alkoxy or an unsubstituted or substituted hydroxyalkoxy; and $R_2$ is COOH, COO-Glucoronide or COO-Sulfate.

Examples of compounds having the above-identified formula that can be used in this method include, but are not limited to, 2-[3-cyano-4-(2-methylpropoxy)phenyl]-4-methylthiazole-5-carboxylic acid, 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid or pharmaceutically acceptable salts thereof.

In yet still another further embodiment, the present invention relates to a method of reducing the incidence of kidney stone attacks in a subject suffering from hyperuricemia. The method involves the step of administering to the subject a therapeutically effective amount of at least one compound, wherein said at least one compound has the following formula:

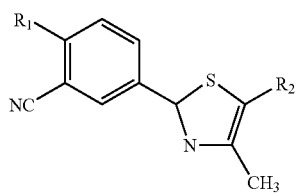

wherein $R_1$ is a hydroxyl group, an unsubstituted or substituted $C_1$-$C_{10}$ alkoxy or an unsubstituted or substituted hydroxyalkoxy; and $R_2$ is COOH, COO-Glucoronide or COO-Sulfate.

Examples of compounds having the above-identified formula that can be used in this method include, but are not limited to, 2-[3-cyano-4-(2-methylpropoxy)phenyl]-4-methylthiazole-5-carboxylic acid, 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid or pharmaceutically acceptable salts thereof.

In yet another embodiment, the present invention relates to a method for preventing kidney stone attacks in a subject having a history of nephrolithiasis. The method involves the step of administering to the subject a prophylactically effective amount of at least one compound, wherein said at least one compound has the following formula:

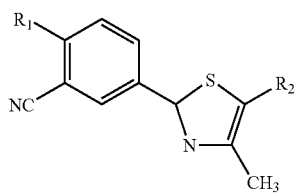

wherein $R_1$ is a hydroxyl group, an unsubstituted or substituted $C_1$-$C_{10}$ alkoxy or an unsubstituted or substituted hydroxyalkoxy; and $R_2$ is COOH, COO-Glucoronide or COO-Sulfate.

Examples of compounds having the above-identified formula that can be used in this method include, but are not limited to, 2-[3-cyano-4-(2-methylpropoxy)phenyl]-4-methylthiazole-5-carboxylic acid, 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid, or pharmaceutically acceptable salts thereof.

DETAILED DESCRIPTION OF THE PRESENT INVENTION

As mentioned briefly above, the present invention relates to methods for treating nephrolithiasis in a subject in need of treatment thereof. In addition, the present invention also relates to methods of reducing the number of kidney stone attacks in a subject suffering from nephrolithiasis or hyperuricemia. Moreover, the present invention also relates to preventing kidney stone attacks in a subject suffering from nephrolithiasis or hyperuricemia. The methods mentioned above will generally comprise administering to a subject in need of such therapy a therapeutically or prophylactically effective amount of at least one xanthine oxidoreductase inhibiting compound or salt thereof to said subject.

Subjects with nephrolithiasis have suffered at least one kidney stone (of any type such as a calcium stone, uric acid stone, cystine stone and/or struvite stone) at one point in their medical history. Ten (10) to twenty-five percent (25%) of subjects with hyperuricemia suffer at least one kidney stone (usually a uric acid stone) at some point in time. As mentioned briefly previously, a number of different drugs are known to be useful for treating subjects having a history of nephrolithiasis. However, these drugs are also known to cause significant side effects. The inventors of the present invention have found that a class of compounds known as xanthine oxidoreductase inhibitors can be used to treat subjects suffering from nephrolithiasis.

As used herein, the term "subject" refers to an animal, preferably a mammal, including a human or non-human. The terms patient and subject may be used interchangeably herein. As used herein, the term "kidney stone(s)" refers to calculi (stones) having any composition. Examples of kidney stones include, but are not limited to, calcium stones, such as calcium oxalate stones, calcium phosphate stones and calcium oxalate and phosphate stones, uric acid stones, cystine stones and struvite stones. As used herein, the term "pharmaceutically acceptable" includes moieties or compounds that are, within the scope of sound medical judgment, suitable for use in contact with the tissues of humans and lower animals without undue toxicity, irritation, allergic response, and the like, and are commensurate with a reasonable benefit/risk ratio. By a "therapeutically effective amount" or "prophylactically effective amount" of a drug (namely, at least one xanthine oxidoreductase inhibitor or a salt thereof) is meant a nontoxic but sufficient amount of the drug to provide the desired effect. The amount of drug that is "effective" or "prophylactic" will vary from subject to subject, depending on the age and general condition of the individual, the particular drug or drugs, and the like. Thus, it is not always possible to specify an exact "therapeutically effective amount" or a "prophylactically effective amount". However, an appropriate "therapeutically effective amount" or "prophylactically effective amount" in any individual case may be determined by one of ordinary skill in the art.

As used herein, the term "xanthine oxidoreductase inhibitor" refers to any compound that (1) is an inhibitor of xanthine oxidoreductase; (2) chemically, does not contain a purine ring in its structure (i.e. is a "non-purine"); and (3) does not have an effect at a therapeutically effective amount in a subject on the activity of any of the following enzymes involved in purine and pyrimidine metabolism: guanine deaminase, hypoxanthine-guanine phosphoribosyltransferse, purine nucleotide phosphorylase, orotate phosphoribosyltransferase or orotidine-5-monophosphate decarboxylase (i.e., meaning that it is "selective" for none of the enzymes involved in purine and pyrimidine metabolism). Assays for determining the activity for each of the above-described enzymes is described in Yasuhiro Takano, et al., *Life Sciences,* 76:1835-1847 (2005). Examples of xanthine oxidoreductase inhibitors include, but are not limited to, 2-[4-(2-carboxypropoxy)-3-cyanophenyl]-4-methyl-5-thiazolecarboxylic acid and compounds having the following formula:

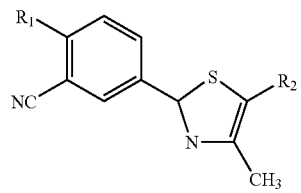

wherein $R_1$ is a hydroxyl group, an unsubstituted or substituted $C_1$-$C_{10}$ alkoxy or an unsubstituted or substituted hydroxyalkoxy; and $R_2$ is COOH, COO-Glucoronide, COO-Sulfate.

Solvates and prodrugs of the xanthine oxidoreductase inhibitors having the above described formula are also contemplated for use in the methods of the present invention. As used herein, the term "prodrug" refers to a derivative of the compounds shown in the above-described formula that have chemically or metabolically cleavable groups and become by solvolysis or under physiological conditions compounds that are pharmaceutically active in vivo. Esters of carboxylic acids are an example of prodrugs that can be used in the methods of the present invention. Methyl ester prodrugs may be prepared by reaction of a compound having the above-described formula in a medium such as methanol with an acid or base esterification catalyst (e.g., NaOH, $H_2SO_4$). Ethyl ester prodrugs are prepared in similar fashion using ethanol in place of methanol.

Examples of compounds having the above formula are: 2-[3-cyano-4-(2-methylpropoxy)phenyl]-4-methylthiazole- 5-carboxylic acid, 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid, 1-(3-cyano-4-(2,2-dimethylpropoxy)phenyl)-1H-pyrazole-4-carboxylic acid or or pharmaceutically acceptable salts thereof.

Methods for making xanthine oxidoreductase inhibiting compounds for use in the methods of the present invention are known in the art and are described, for example, in U.S. Pat. No. 5,614,520. Other xanthine oxidoreductase inhibiting compounds can be found using xanthine oxidoreductase and xanthine in assays to determine if such candidate compounds inhibit conversion of hypoxanthine into xanthine or uric acid. Such assays are well known in the art.

Compositions containing at least one xanthine oxidoreductase inhibiting compound in combination with at least one other pharmaceutical compound are contemplated by the present invention. Using the excipients and dosage forms described below, formulations containing such combinations are a matter of choice for those skilled in the art. Further, those skilled in the art will recognize that various coatings or other separation techniques may be used in cases where the combination of compounds are incompatible.

Compounds used in accordance with the methods of the present invention can be provided in the form of pharmaceutically acceptable salts derived from inorganic or organic acids. Pharmaceutically acceptable salts are well-known in the art. For example, S. M. Berge et al. describe pharmaceutically acceptable salts in detail in *J. Pharmaceutical Sciences*, 66: 1 et seq. (1977). The salts can be prepared in situ during the final isolation and purification of the compounds or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

The at least one xanthine oxidoreductase inhibiting compound or salts thereof, may be formulated in a variety of ways that is largely a matter of choice depending upon the delivery route desired. For example, solid dosage forms for oral administration include capsules, tablets, pills, powders and granules. In such solid dosage forms, the xanthine oxidoreductase inhibiting compound may be mixed with at least one inert, pharmaceutically acceptable excipient or carrier, such as sodium citrate or dicalcium phosphate and/or a) fillers or extenders, such as, but not limited to, starches, lactose, sucrose, glucose, mannitol and silicic acid; b) binders, such as, but not limited to, carboxymethylcellulose, alginates, gelatin, polyvinylpyrrolidone, sucrose and acacia; c) humectants, such as, but not limited to glycerol; d) disintegrating agents, such as, but not limited to, agar-agar, calcium carbonate, potato or tapioca starch, alginic acid, certain silicates and sodium carbonate; e) solution retarding agents, such as, but not limited to, paraffin; f) absorption accelerators, such as, but not limited to, quaternary ammonium compounds; g) wetting agents, such as, but not limited to, cetyl alcohol and glycerol monostearate; h) absorbents, such as, but not limited to, kaolin and bentonite clay; and i) lubricants, such as, but not limited to, talc, calcium stearate, magnesium stearate, solid polyethylene glycols, sodium lauryl sulfate and mixtures thereof.

Solid compositions of a similar type may also be employed as fillers in soft and hard-filled gelatin capsules using such excipients as lactose or milk sugar as well as high molecular weight polyethylene glycols and the like.

The solid dosage forms of tablets, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

Liquid dosage forms for oral administration include pharmaceutically acceptable emulsions, solutions, suspensions, syrups and elixirs. In addition to the xanthine oxidoreductase inhibiting compounds, the liquid dosage forms may contain inert diluents commonly used in the art such as, for example, water or other solvents, solubilizing agents and emulsifiers, such as, but not limited to, ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

The compositions can also be delivered through a catheter for local delivery at a target site, via an intracoronary stent (a tubular device composed of a fine wire mesh), or via a biodegradable polymer.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include, but are not limited to, water, ethanol, polyols (propylene glycol, polyethylene glycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form can be brought about by the use of agents delaying absorption, for example, aluminum monostearate and gelatin.

Suspensions, in addition to the active compounds (i.e., xanthine oxidoreductase inhibiting compounds or salts thereof), may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Proper fluidity can be maintained, for example, by the use of coating materials such as lecithin, by the maintenance of the required particle size in the case of dispersions and by the use of surfactants.

In some cases, in order to prolong the effect of the drug (i.e. xanthine oxidoreductase inhibiting compounds or salts thereof), it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Dosage forms for topical administration of the compounds of this present invention include powders, sprays, ointments and inhalants. The active compound(s) is mixed under sterile conditions with a pharmaceutically acceptable carrier and any needed preservatives, buffers or propellants which can be required. Opthalmic formulations, eye ointments, powders and solutions are also contemplated as being within the scope of this invention.

It will be understood that formulations used in accordance with the present invention generally will comprise a therapeutically effective amount of one or more xanthine oxidoreductase inhibiting compounds. The phrase "therapeutically effective amount" as used herein means a sufficient amount of, for example, the composition, xanthine oxidoreductase inhibiting compound, or formulation necessary to treat the desired disorder, at a reasonable benefit/risk ratio applicable to any medical treatment. As with other pharmaceuticals, it will be understood that the total daily usage of a pharmaceutical composition of the invention will be decided by a patient's attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time administration, route of administration, and rate of excretion of the specific compound employed; the duration of the treatment; drugs used in combination or coincidental with the specific compound employed; and other factors known to those of ordinary skill in the medical arts. For example, it is well within the skill of the art to start doses of the compound at levels lower than required to achieve the desired therapeutic effect and to gradually increase the dosage until the desired effect is achieved.

Formulations of the present invention are administered and dosed in accordance with sound medical practice, taking into account the clinical condition of the individual patient, the site and method of administration, scheduling of administration, and other factors known to medical practitioners.

Therapeutically effective amounts for purposes herein thus can readily be determined by such considerations as are known in the art. The daily pharmaceutically effective amount of the xanthine oxidoreductase inhibiting compounds administered to a patient in single or divided doses range from about 0.01 to about 750 milligram per kilogram of body weight per day (mg/kg/day). More specifically, a patient may be administered from about 5.0 mg to about 300 mg once daily, preferably from about 20 mg to about 240 mg once daily and most preferably from about 40 mg to about 120 mg once daily of xanthine oxidoreductase inhibiting compounds.

By way of example, and not of limitation, examples of the present invention will now be given.

EXAMPLE 1

Eighteen (18) hyperuricemic subjects with gout and a history of nephrolithiasis in their medical history were examined. Specifically, these eighteen subjects were part of a double-blind (DB) four (4) week study in which they received 40, 80 or 120 mg once daily (hereinafter referred to as "QD") of 2-[3-cyano-4-(2-methylpropoxy)phenyl]-4-methylthiazole-5-carboxylic acid (hereinafter called "febuxostat") or a placebo, followed by an open-label (OL) extension study of febuxostat 80 mg QD titrated to 40 mg or 120 mg QD of febuxostat based on serum uric acid levels and adverse events.

The subjects were predominantly male (specifically, sixteen (16)) Caucasian, with a mean age of 55 years. Eleven (11) of the subjects had gout for more than 10 years, five (5) subjects had gout for between 5 to 10 years and two (2) subjects had gout for between 1 to 5 years. Overall, subject experienced between 1 and 20 attacks over a 2 to 45 year period prior to baseline. Twelve (12) of the subjects were classified as renally impaired (their creatinine clearance was <80 ml/minute). Six (6) subjects were considered to be uric acid overproducers (urinary uric acid excretion was greater than 800 mg/day). Comorbid conditions in these subjects included the following: hyperlipidemia (78%), hypertension (72%), obesity (56%) and coronary artery disease (17%). The mean serum urate for these subjects at baseline was 10.0 mg/dL.

All subjects completed this DB study. Fifteen (15) subjects rolled over to the OL study with thirteen (13) completing treatment for a duration of greater than thirty (30) months. The majority of subjects (11/13) received daily febuxostat in the amount of 80 mg QD with two (2) subjects having their dose titrated to febuxostat 120 mg QD as per study protocol because of a post-baseline serum urate of ≥6.0 mg/dL.

The mean serum urate for these subjects at their last visit was 5.2 mg/dL and the mean reduction in serum urate was 47%.

During the DB and OL portions of the study, with greater than thirty (30) months of febuxostat treatment, kidney stones were reported by two (2) subjects out of the 18 subjects who reported nephrolithiasis in their medical history. The first subject reported two (2) occurrences of kidney stones. The first stone occurred while this subject was receiving placebo in the DB study. The second stone occurred on day 38 of the OL study while the subject was receiving 80 mg QD of febuxostat. The second subject reported a kidney stone while receiving 80 mg QD of febuxostat on day 977 of the study. Further analysis revealed that all three (3) kidney stones reported during this study were determined to be calcium oxalate stones. None of the two (2) subjects withdrew from the study as a result of the kidney stones.

Adverse events were self-limiting and transient.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

What is claimed is:

1. A method for treating nephrolithiasis in a subject in need of treatment thereof, the method comprising the step of:
administering to the subject a therapeutically effective amount of at least one compound, wherein said at least one compound is a xanthine oxidoreductase inhibitor or a pharmaceutically acceptable salt thereof, wherein the xanthine oxidoreductase does not contain a purine ring in its structure, wherein the xanthine oxidoreductase inhibitor is 2-[3-cyano-4-(2-methylpropoxy)phenyl]-4-methylthiazole-5-carboxylic acid and, wherein the therapeutically effective amount is from about 5 mg to about 300 mg.

2. A method for reducing the number of incidence of kidney stone attacks in a subject having a history of nephrolithiasis, the method of comprising the step of:
administering to the subject a therapeutically effective amount of a compound wherein said at least one compound is a xanthine oxidoreductase inhibitor or a pharmaceutically acceptable salt thereof, wherein the xanthine oxidoreductase inhibitor is 2-[3-cyano-4-(2-methylpropoxy)phenyl]-4-methylthiazole-5-carboxylic acid and, wherein the therapeutically effective amount is from about 5 mg to about 300 mg.

* * * * *